(12) United States Patent
Wiederin et al.

(10) Patent No.: US 8,679,235 B1
(45) Date of Patent: Mar. 25, 2014

(54) DUAL-CYCLONIC SPRAY CHAMBER

(75) Inventors: Daniel R. Wiederin, Omaha, NE (US);
Kyle W. Uhlmeyer, Omaha, NE (US);
James W. Harris, Ames, NE (US)

(73) Assignee: Elemental Scientific, Inc., Omaha, NE (US)

( * ) Notice: Subject to any disclaimer, the term of this patent is extended or adjusted under 35 U.S.C. 154(b) by 106 days.

(21) Appl. No.: 13/238,237

(22) Filed: Sep. 21, 2011

Related U.S. Application Data

(60) Provisional application No. 61/385,012, filed on Sep. 21, 2010.

(51) Int. Cl.
*B01D 45/12* (2006.01)

(52) U.S. Cl.
USPC .......... 95/271; 55/322; 55/326; 55/337; 55/345; 55/349; 55/346; 55/343; 55/459.1

(58) Field of Classification Search
USPC .......... 55/322, 326, 337, 345, 349, 346, 343, 55/459.1; 95/271
See application file for complete search history.

(56) References Cited

U.S. PATENT DOCUMENTS 7,390,339 B1 * 6/2008 Warrick et al. ............... 55/346

* cited by examiner

*Primary Examiner* — Dung H Bui
(74) *Attorney, Agent, or Firm* — Advent, LLP

(57) ABSTRACT

A dual-cyclonic spray chamber apparatus is described. In one or more implementations, the dual-cyclonic spray chamber apparatus includes a first cyclonic spray chamber for receiving an aerosol and conditioning the aerosol to separate a first conditioned portion of the aerosol from a second portion of the aerosol. The first cyclonic spray chamber defines a first chamber interior and comprises an input port in fluid communication with the first chamber interior. The dual-cyclonic spray chamber apparatus also includes a second cyclonic spray chamber coupled with the first cyclonic spray chamber for receiving the first conditioned portion of the aerosol and further conditioning the first conditioned portion of the aerosol. The second cyclonic spray chamber defines a second chamber interior and comprises an output port for expelling a first further conditioned portion of the first conditioned portion of the aerosol from the second chamber interior.

11 Claims, 8 Drawing Sheets

Figure 3:
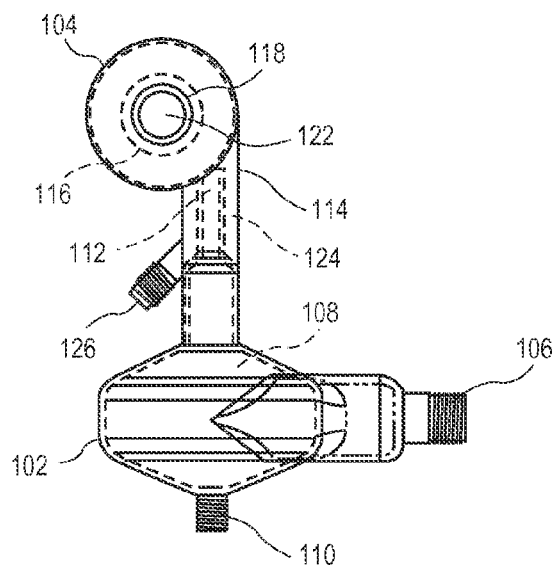

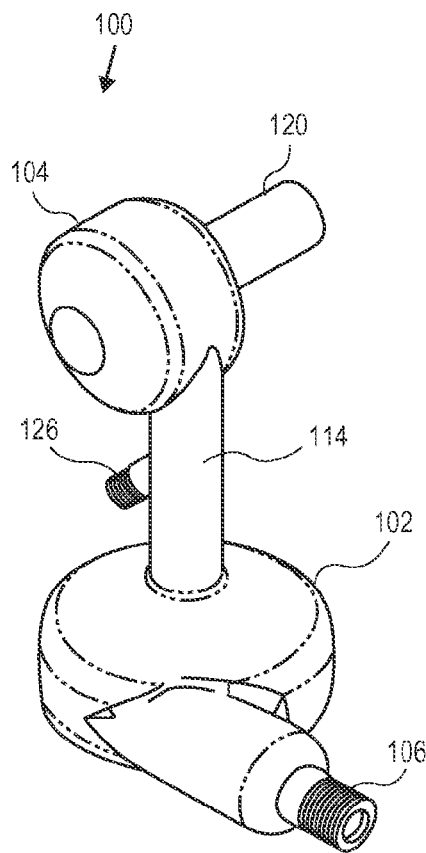
FIG. 1
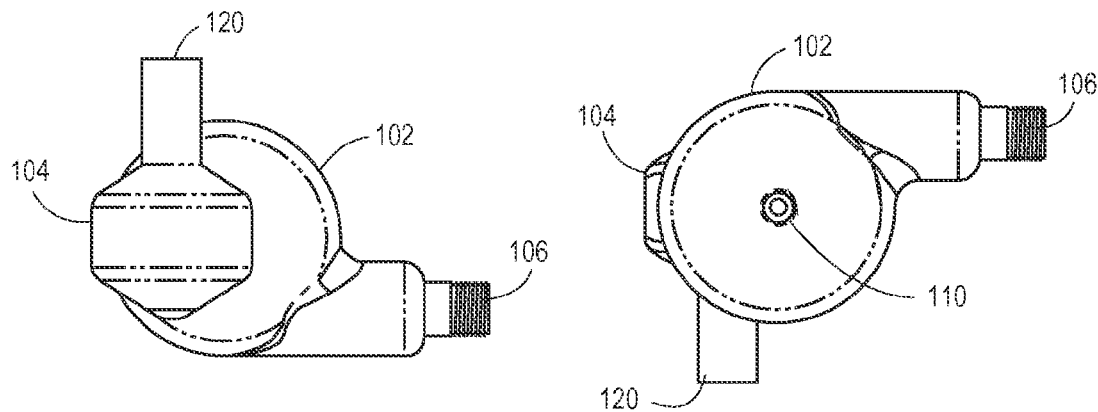
FIG. 2A  FIG. 2B

DUAL-CYCLONIC SPRAY CHAMBER

CROSS-REFERENCE TO RELATED APPLICATIONS

The present application claims the benefit of 35 U.S.C. §119(e) of U.S. Provisional Application Ser. No. 61/385,012, filed Sep. 21, 2010, and titled "DUAL-CYCLONIC SPRAY CHAMBER APPARATUS," which is herein incorporated by reference in its entirety.

BACKGROUND

Analytical equipment, including Mass Spectrometers (MS) and Atomic Emission Spectrometers (AES), are utilized for detecting trace elements of species in samples. Inductively Coupled Plasma MS (ICP-MS) and Inductively Coupled Plasma AES (ICP-AES) are two sample analysis systems used by laboratories for the determination of trace element concentrations and isotope ratios in liquid samples. ICP spectrometry employs electromagnetically generated partially ionized plasma, which can reach temperatures of approximately seven thousand Kelvin (7,000 K). When a sample is introduced to the plasma, the high temperature causes sample atoms to become ionized or emit light. Since each chemical element and ratios thereof produces a characteristic mass or emission spectrum, measuring the spectra of the emitted mass or light allows for the determination of the elemental composition of the original sample.

SUMMARY

A dual-cyclonic spray chamber apparatus is described. In one or more implementations, the dual-cyclonic spray chamber apparatus includes a first cyclonic spray chamber for receiving an aerosol and conditioning the aerosol to separate a first conditioned portion of the aerosol from a second portion of the aerosol. The first cyclonic spray chamber defines a first chamber interior and comprises an input port in fluid communication with the first chamber interior for receiving the aerosol to be conditioned by the first cyclonic spray chamber. The dual-cyclonic spray chamber apparatus also includes a second cyclonic spray chamber coupled with the first cyclonic spray chamber for receiving the first conditioned portion of the aerosol and further conditioning the first conditioned portion of the aerosol to separate a first further conditioned portion of the first conditioned portion of the aerosol from a second conditioned portion of the first conditioned portion of the aerosol. The second cyclonic spray chamber defines a second chamber interior and comprises an output port for expelling the first further conditioned portion of the first conditioned portion of the aerosol from the second chamber interior.

The dual-cyclonic spray chamber apparatus may further include a drain port in fluid communication with the first chamber interior for removing the second portion of the aerosol from the first cyclonic spray chamber. The dual-cyclonic spray chamber apparatus may also include a baffle at least partially disposed within the second chamber interior, where the baffle defines an interior portion for receiving the first further conditioned portion of the first conditioned portion of the aerosol. The dual-cyclonic spray chamber apparatus may further include a linking chamber for coupling the first cyclonic spray chamber to the second cyclonic spray chamber. The linking chamber may comprise a taper and may form an annular drain portion for removing the second conditioned portion of the first conditioned portion of the aerosol from the second cyclonic spray chamber. The volume defined by the first chamber interior may be greater than the volume defined by the second chamber interior.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 1 is an isometric view illustrating a dual-cyclonic spray chamber apparatus in accordance with an example implementation of the present disclosure.

FIG. 2A is a top plan view of the dual-cyclonic spray chamber apparatus illustrated in FIG. 1.

FIG. 2B is a bottom plan view of the dual-cyclonic spray chamber apparatus illustrated in FIG. 1.

FIG. 3 is a side elevation view of the dual-cyclonic spray chamber apparatus illustrated in FIG. 1.

FIG. 4 is a cross-sectional side elevation view of the dual-cyclonic spray chamber apparatus illustrated in FIG. 1.

FIG. 5 is a cross-sectional isometric view of the dual-cyclonic spray chamber apparatus illustrated FIG. 1.

FIG. 6 is an example of output signal intensity over time for a sample tested utilizing a dual-cyclonic spray chamber apparatus for sample preparation in accordance with an example implementation of the present disclosure.

FIG. 7 is a graph illustrating several output signals from a sample tested in a baffled cyclonic spray chamber, such as a second cyclonic spray chamber included with a dual-cyclonic spray chamber apparatus.

FIG. 8 is a graph illustrating several output signals from a sample tested in a non-baffled cyclonic spray chamber, such as a first cyclonic spray chamber included with a dual-cyclonic spray chamber apparatus.

FIG. 9 is a graph illustrating several output signals from a sample tested in a dual-cyclonic spray chamber apparatus in accordance with an example implementation of the present disclosure.

FIG. 10 is a detection limit comparison chart illustrating a comparison of furnace element detection limits for a baffled cyclonic spray chamber and a dual-cyclonic spray chamber.

DETAILED DESCRIPTION

Overview

When a sample is introduced to plasma in ICP spectrometry, the high temperature causes sample atoms to become ionized or emit light. Measuring the spectra of the emitted mass or light allows for the determination of the elemental composition of the sample. Sample analysis systems may employ a sample introduction system for conditioning a sample prior to introduction into the analytical equipment. For example, a sample introduction system may withdraw an aliquot of a liquid sample from a sample container and transport the aliquot to a nebulizer that converts the aliquot into a polydisperse aerosol suitable for ionization in plasma by the ICP spectrometry instrumentation. Such conversion may take place in a spray chamber prior to introduction to the plasma. The nebulized sample may include a distribution of large and small aerosol particles. The large aerosol particles may inhibit signal stability and intensity of the nebulized sample when analyzed. The spray chamber can be configured to remove the larger aerosol particles to improve signal stability and intensity of the nebulized sample.

One particular spray chamber design is known as a cyclonic spray chamber, which causes the nebulized sample to swirl within the chamber. The larger particles collide with the walls of the chamber and are drained from the chamber, whereas the smaller particles are expelled from the chamber through an outlet, typically located at a vertical end of the chamber. The cyclonic spray chamber may be modified to include a baffle that serves as an additional region of impact for the larger particles. However, one problem with a baffled cyclonic spray chamber is that signals from the analyzed sample may be lower than in a non-baffled spray chamber. This may be due to the nebulized sample being introduced in close proximity to the baffle, which may cause smaller aerosol particles to impact the baffle. Further, a non-baffled cyclonic spray chamber may provide less short term stability than a baffled cyclonic spray chamber, and may lead to a build-up of liquid in the ICP torch injector, which can reduce signal quality as well as extinguish the ICP plasma.

Accordingly, the present disclosure is directed to a dual-cyclonic spray chamber apparatus that can provide separation of large aerosol particles from smaller aerosol particles using two or more cyclonic spray chambers. The dual-cyclonic spray chamber apparatus can provide short-term stability by mixing using two or more cyclonic spray chambers, and long-term plasma stability by preventing the formation of droplets in a torch injector base. The dual-cyclonic spray chamber apparatus includes a first cyclonic spray chamber having an input port for receiving an aerosol to be conditioned in the interior of the first chamber and a second cyclonic spray chamber coupled with the first cyclonic spray chamber (e.g., via a linking chamber). The second cyclonic spray chamber may include a baffle disposed in the interior of the second chamber and coupled with an output port for supplying a portion of the conditioned aerosol from the first chamber via, for example, an ICP torch injector. In implementations, the input port of the first cyclonic spray chamber may be generally orthogonal to the output port of the second cyclonic spray chamber. In the following discussion, example implementations of dual-cyclonic spray chambers are described.

Example Implementations

FIGS. 1 through 5 illustrate dual-cyclonic spray chamber apparatus in accordance with example implementations of the present disclosure. As shown, a dual-cyclonic spray chamber apparatus 100 includes a first cyclonic spray chamber 102 coupled with a second cyclonic spray chamber 104. The first cyclonic spray chamber 102 defines a chamber interior 108, and may include an input port 106, a drain port 110, and an output port 112. The input port 106 can be configured to couple with, for instance, a nebulizer in order to accept an aerosol produced from the nebulizer. For example, the input port 106 can include a threaded connector, quick-connect type coupler hardware, and so forth.

The first cyclonic spray chamber 102 is configured to condition the aerosol by separating relatively large aerosol particles from smaller aerosol particles by allowing the larger aerosol particles to impact with the walls of the chamber interior 108. In particular, the input port 106 is configured to receive an aerosol to be conditioned in the chamber interior 108 to produce a first conditioned portion of the aerosol (e.g., the smaller aerosol particles) and a second portion of the aerosol (e.g., the larger aerosol particles). The second portion of the aerosol may then be removed from the chamber interior 108. The output port 112 is configured to pass the first conditioned portion of the aerosol from the chamber interior 108 to the second cyclonic spray chamber 104. The drain port 110 facilitates removal of the second portion of the aerosol from the chamber interior 108. For instance, the drain port 110 can remove larger aerosol particles to reduce the build-up of aerosol particles within the dual-cyclonic spray chamber apparatus 100. Thus, the dual-cyclonic spray chamber apparatus 100 may prevent fluid from accumulating within an analytic system, which may include an ICP torch susceptible to error, extinguishing, and so forth, by excess fluid within the system.

The second cyclonic spray chamber 104 may be coupled with the output port 112 of the first cyclonic spray chamber 102 via a linking chamber 114. The second cyclonic spray chamber 104 may include a second chamber interior 116, a baffle 118, and an output port 120. The second chamber interior 116 is configured to receive the first conditioned portion of the aerosol from the output port 112. For instance, the aerosol may swirl within the chamber interior 108, such as in a substantially circular path, in order to be conditioned. The first conditioned portion may then exit the first cyclonic spray chamber 102 and pass to the second chamber interior 116 via the output port 112. The first conditioned portion may then swirl within the second chamber interior 116, so as to be further conditioned in the second cyclonic spray chamber 104. This dual-cyclonic action may result in the stabilization of a resultant signal (while maintaining signal intensity) from the analysis of the portion of the aerosol exiting the dual-cyclonic spray chamber apparatus 100 via the output port 120.

Figure 4:
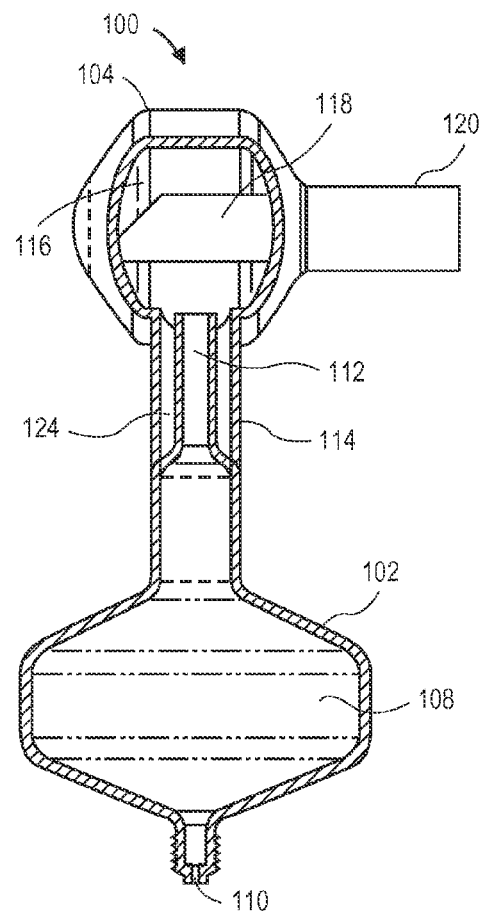
Figure 5:
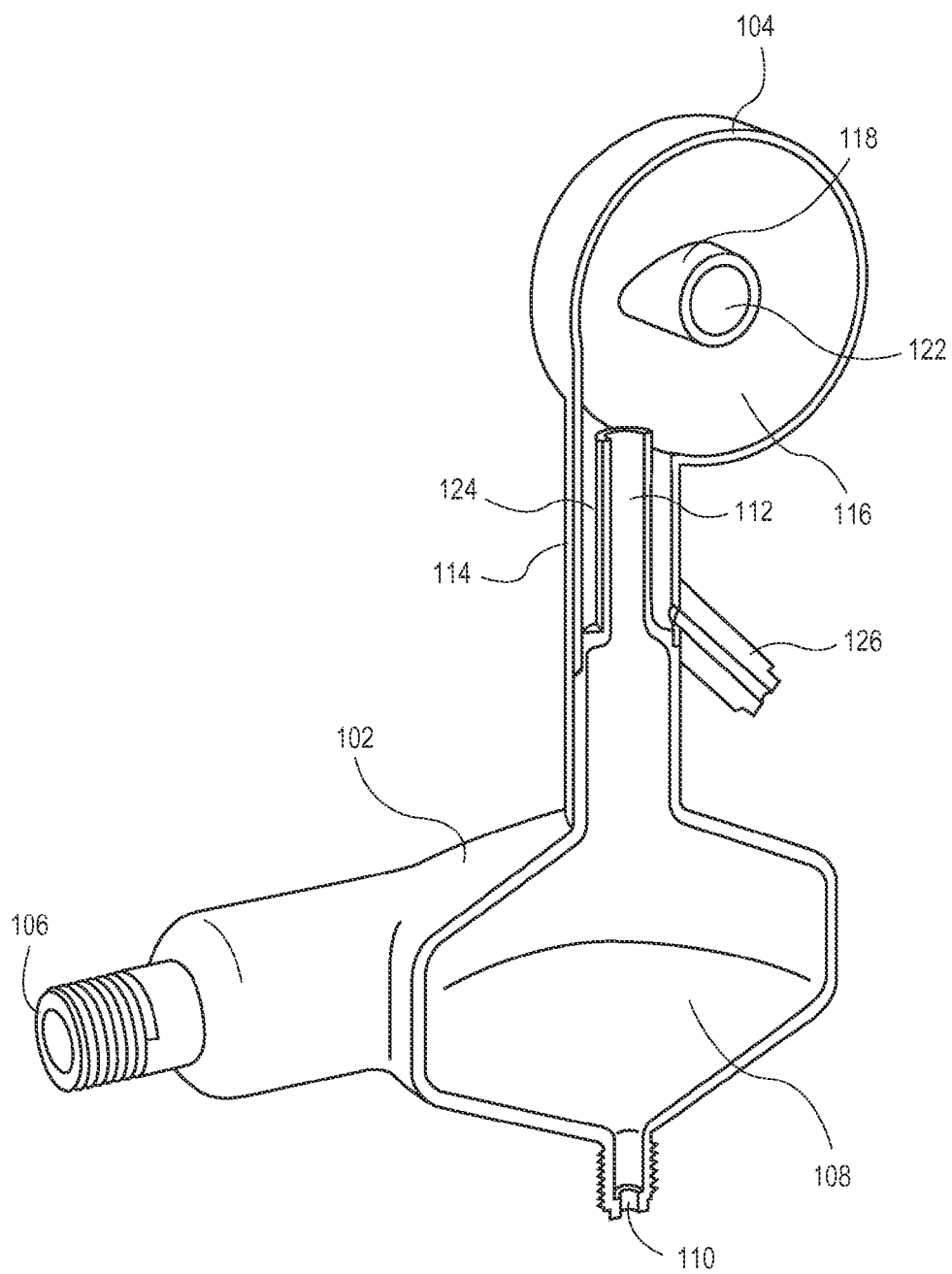

Referring now to FIGS. 4 and 5, the second cyclonic spray chamber 104 may be a baffled cyclonic spray chamber. In a particular embodiment, the baffle 118 is at least partially disposed within the chamber interior 118 and is coupled with the output port 120, so that the baffle 118 and the output port 120 form a continuous path through which at least a first further conditioned portion of the first conditioned portion of the aerosol may pass. For example, the baffle 118 may define an interior portion 122 (e.g., a substantially cylindrical portion) configured to receive at least a portion of the first conditioned portion of the aerosol for expelling the portion of the first conditioned portion from the second chamber interior 116 via the output port 120.

Figure 6:
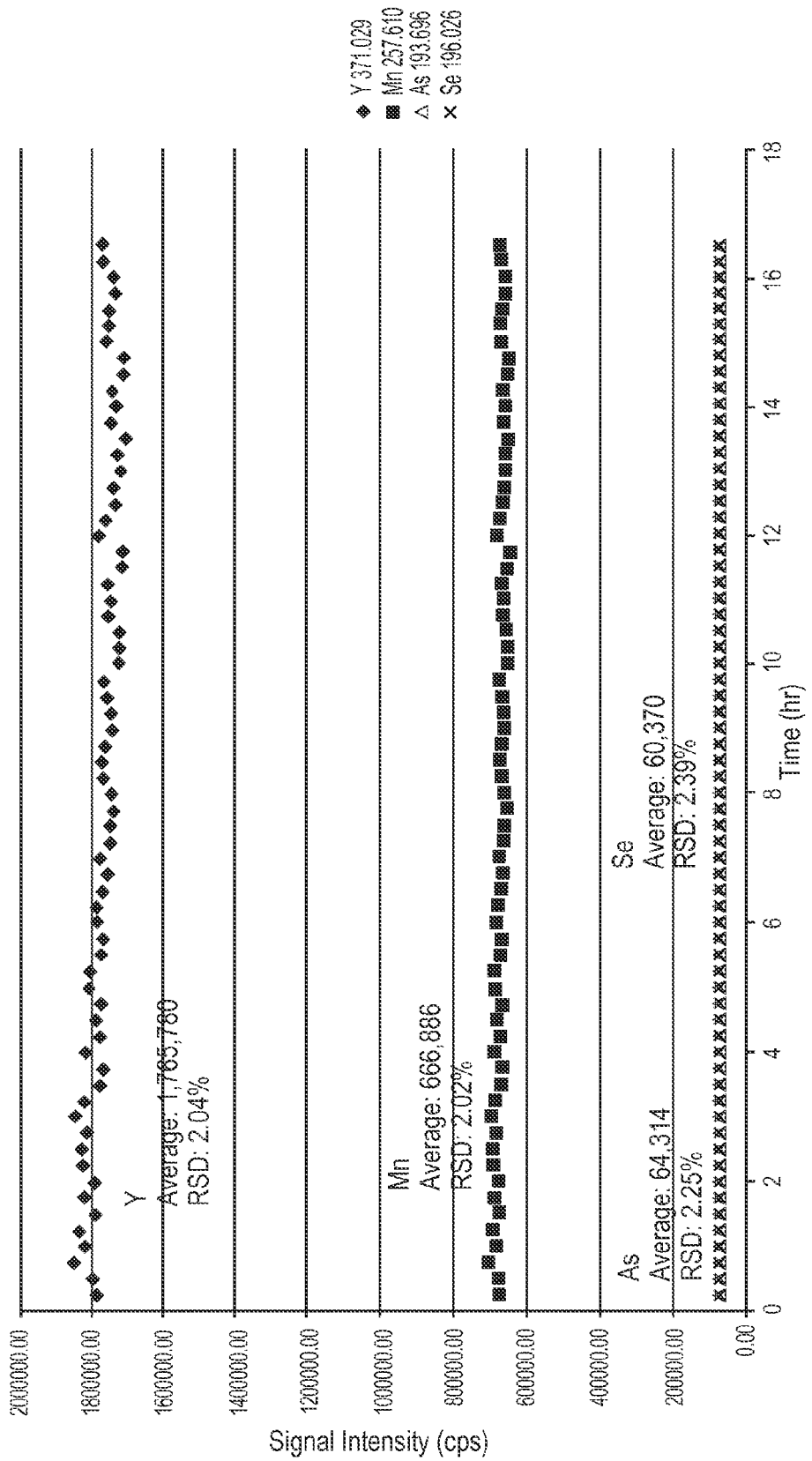
Figure 7:
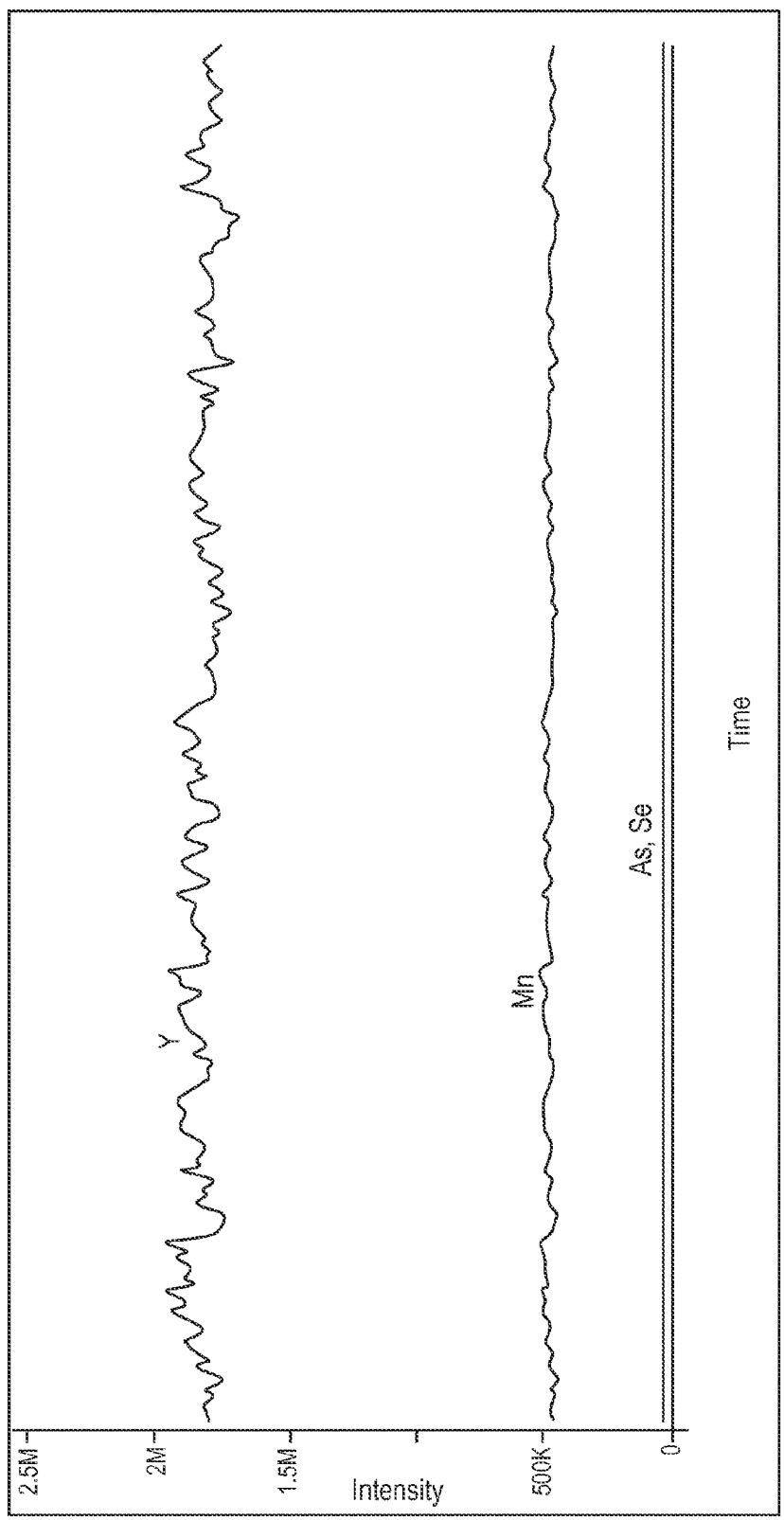
Figure 8:
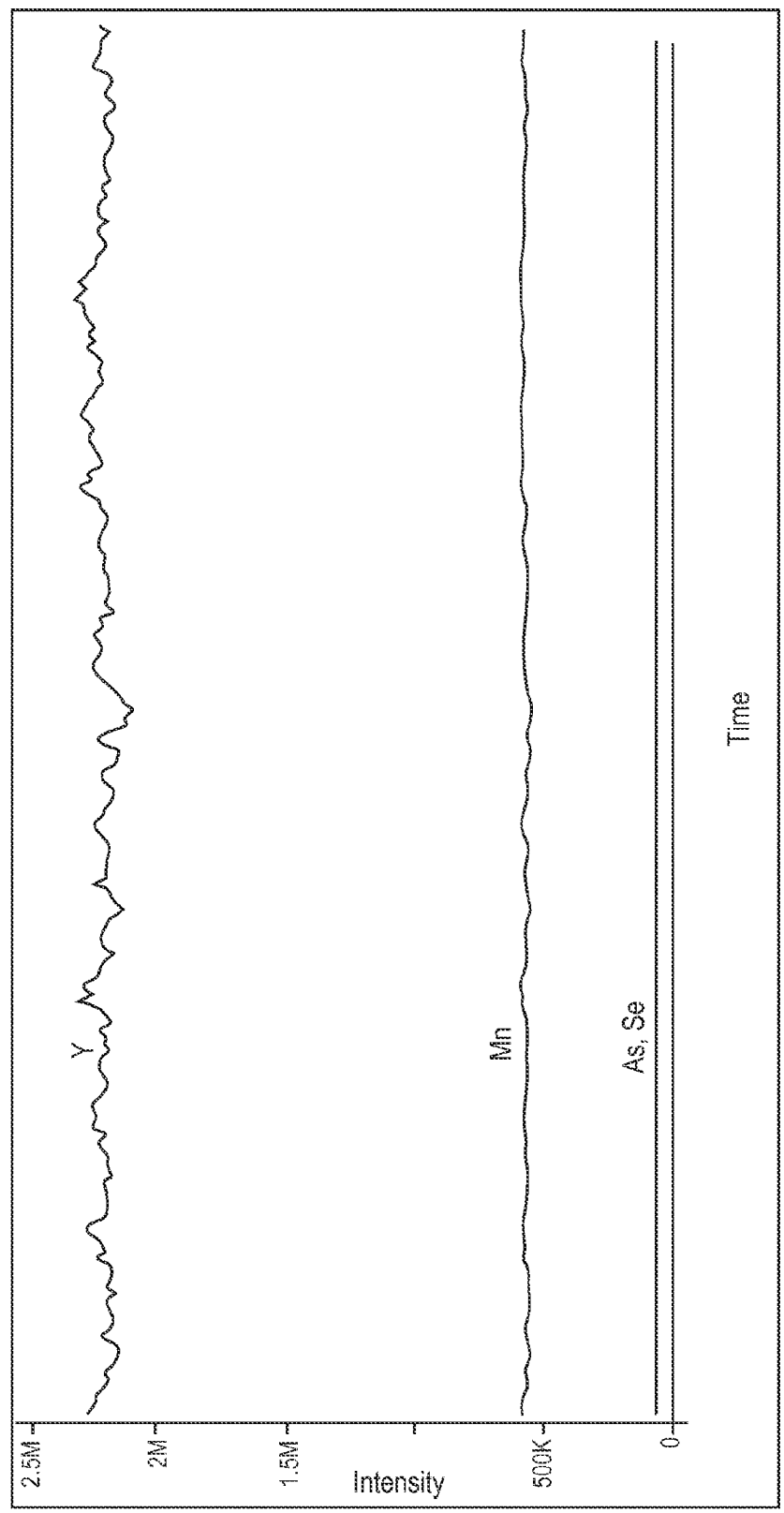
Figure 9:
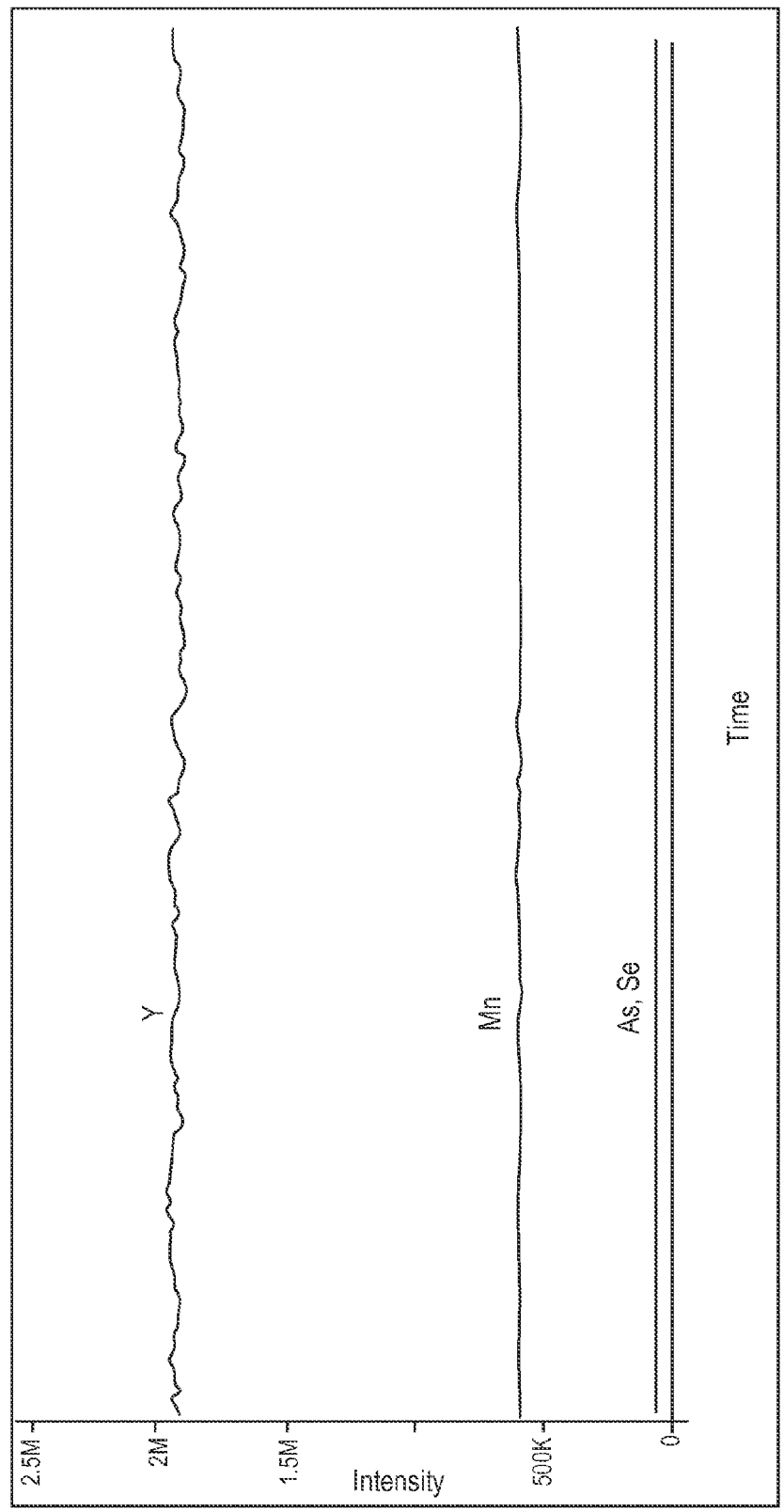

The dual-cyclonic spray chamber apparatus 100 may be configured so that the volume defined by the first chamber interior 108 which is greater than the volume defined by the second chamber interior 116. When the second portion of the aerosol is drained from the first cyclonic spray chamber 102 (e.g., via the drain port 110), the first conditioned portion of the aerosol may occupy less volume when passed to the second cyclonic spray chamber 104 for further conditioning. By providing a second chamber interior 116 having a smaller volume than that of the chamber interior 108, the dual-cyclonic spray chamber apparatus 100 may have a reduced dead (unused) volume when compared to a configuration having equal volumes for the chamber interior 108 and the second chamber interior 116. A reduced dead volume may require less time for a sample signal to stabilize during analysis with analytic instrumentation. FIG. 6 illustrates an example of output signal intensity over time for a sample tested utilizing a dual-cyclonic spray chamber apparatus for sample preparation. The sample was analyzed over an approximately sixteen (16) hour period utilizing an ICP-AES. The analysis detected amounts of yttrium (Y), manganese (Mn), arsenic (As), and selenium (Se) in the sample, with the intensities detected as shown in FIG. 6. The stability of the signal of each of the four detected species can be seen with respect to the Relative Standard Deviation (RSD), which ranges from 2.02% (for manganese) to 2.39% (for selenium) in FIG. 6.

As shown in FIGS. 1 through 5, the input port 106 may be positioned generally orthogonally to the output port 120. In one particular implementation, the second cyclonic spray chamber 104 can be offset with respect to the output port 112, such that the first conditioned portion of the aerosol flowing from the output port 112 is directed tangentially with respect to the walls of the second chamber interior 116. The portion of the aerosol entering the interior portion 122 of the baffle 118 may then exit the second cyclonic spray chamber 104 via the output port 120 in an orientation that is orthogonal to the orientation of the input port 106. Since the baffle 118 is included in the second cyclonic spray chamber 104, the baffle 118 is separated from the input port 106, which is configured to couple with a nebulizer in order to accept an aerosol produced from the nebulizer. The separation between the baffle and the input port 106 in the dual-cyclonic spray chamber apparatus 100 may alleviate signal loss associated with aerosol impacting the baffle directly after being introduced to a spray chamber (such as when solely using a baffled spray chamber).

The linking chamber 114 of the dual-cyclonic spray chamber apparatus 100 may be disposed between the first cyclonic spray chamber 102 and the second cyclonic spray chamber 104. The output port 112 may be disposed at least partially within the linking chamber 114. For instance, the output port 112 may be positioned approximately concentrically within the linking chamber 114 and may taper within the linking chamber 114, forming a drain portion 124 within the annular space between the output port 112 and the linking chamber 114. The linking chamber 114 may include a drain port 126 coupled with the drain portion 124. The drain port 126 may be configured to pass aerosol particles which were removed from the conditioning of the first conditioned aerosol portion in the second cyclonic spray chamber 104. For example, larger aerosol particles in the first conditioned aerosol portion may impact with the walls of the second chamber interior 116 and/or the baffle, causing the larger particles to enter into the drain portion 124, and subsequently exit the dual-cyclonic spray chamber apparatus 100 via the drain port 126.

Figure 10:
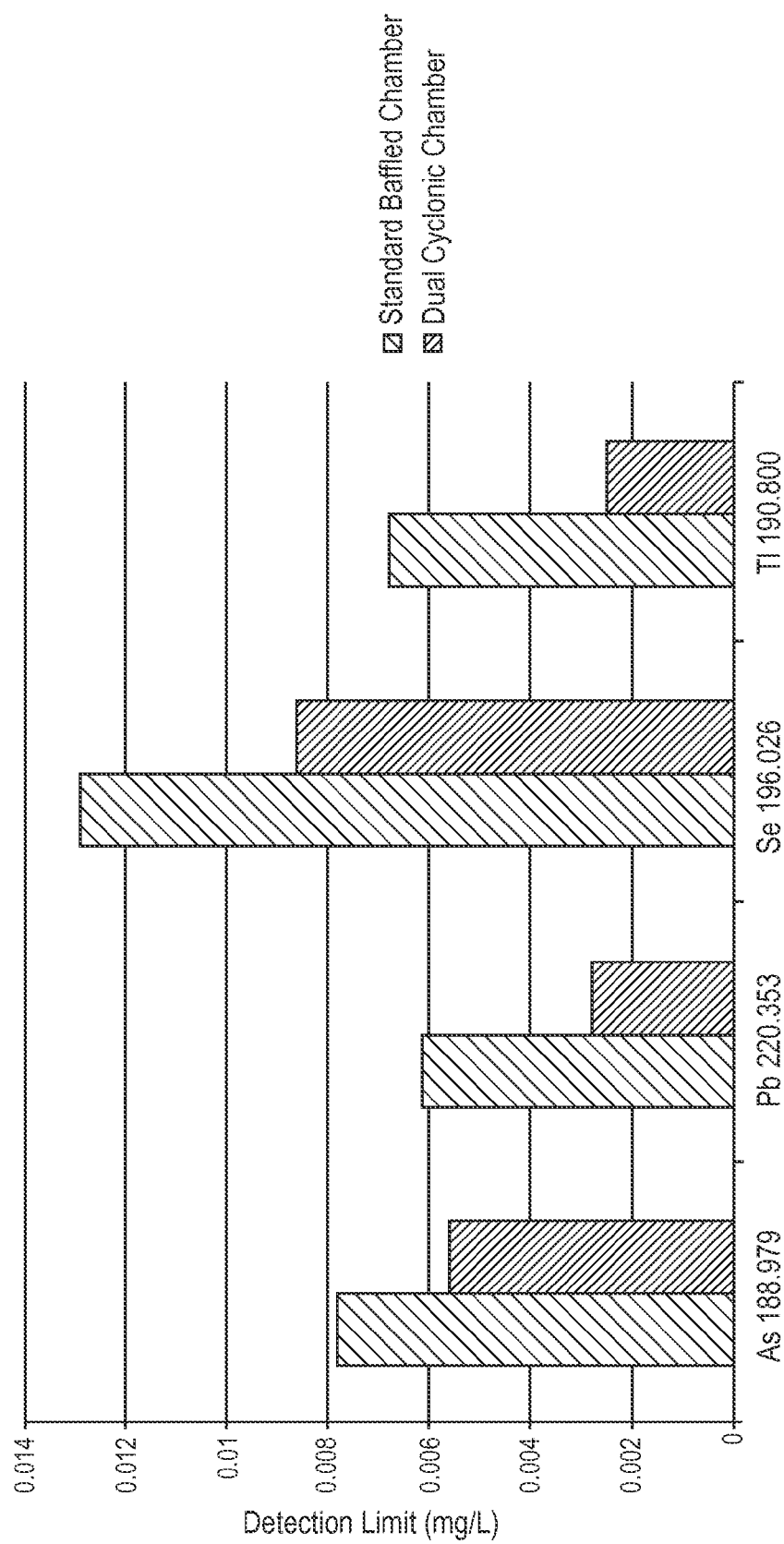

Referring now to FIG. 10, a detection limit comparison was performed to compare furnace element detection limits for a baffled cyclonic spray chamber and a dual-cyclonic spray chamber. The analysis detected amounts of arsenic (As), lead (Pb), selenium (Se), and thallium (Tl) in samples, with the detection limits as shown in FIG. 10. Detection limits can be seen for the baffled cyclonic spray chamber as compared to detection limits for the dual-cyclonic spray chamber. It can be seen that for these two particular configurations, the dual-cyclonic spray chamber provided a lower detection limit threshold for the samples.

It should be noted that while the dual-cyclonic spray chamber apparatus has been described in the accompanying figures as including two cyclonic spray chambers, more than two spray chambers may be provided in accordance with the present disclosure, such as three spray chambers, four spray chambers, and so forth. For example, in some implementations, a dual-cyclonic spray chamber apparatus may include a third cyclonic spray chamber for receiving the first further conditioned portion of the first conditioned portion of the aerosol, and expelling a still further conditioned portion of the first conditioned portion via another outlet port included with the third cyclonic spray chamber. The third cyclonic spray chamber may also be connected to a fourth cyclonic spray chamber, and so forth. Further, the volume of the interior of each successive spray chamber may be reduced from the volume of the previous spray chamber (e.g., as previously described).

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A dual-cyclonic spray chamber apparatus comprising:
   a first cyclonic spray chamber for receiving an aerosol and conditioning the aerosol to separate a first conditioned portion of the aerosol from a second portion of the aerosol;
   a second cyclonic spray chamber coupled with the first cyclonic spray chamber, the second cyclonic spray chamber for receiving the first conditioned portion of the aerosol and further conditioning the first conditioned portion of the aerosol to separate a first further conditioned portion of the first conditioned portion of the aerosol from a second conditioned portion of the first conditioned portion of the aerosol; and
   a linking chamber for coupling the first cyclonic spray chamber to the second cyclonic spray chamber, wherein the linking chamber comprises a taper and forms an annular drain portion for removing the second conditioned portion of the first conditioned portion of the aerosol from the second cyclonic spray chamber.

2. The dual-cyclonic spray chamber apparatus as recited in claim 1, further comprising a baffle at least partially disposed within a second chamber interior defined by the second cyclonic spray chamber, the baffle defining an interior portion for receiving the first further conditioned portion of the first conditioned portion of the aerosol.

3. The dual-cyclonic spray chamber apparatus as recited in claim 1, wherein the first cyclonic spray chamber defines a first chamber interior, the first cyclonic spray chamber comprising an input port in fluid communication with the first chamber interior for receiving the aerosol to be conditioned by the first cyclonic spray chamber and a drain port in fluid communication with the first chamber interior for removing the second portion of the aerosol from the first cyclonic spray chamber, and wherein the second cyclonic spray chamber defines a second chamber interior, the second cyclonic spray chamber comprising an output port for expelling the first further conditioned portion of the first conditioned portion of the aerosol from the second chamber interior.

4. The dual-cyclonic spray chamber apparatus as recited in claim 3, wherein the input port is oriented at least substantially orthogonally to the output port for expelling the first further conditioned portion of the first conditioned portion of the aerosol at least substantially orthogonally to the aerosol received at the first cyclonic spray chamber.

5. The dual-cyclonic spray chamber apparatus as recited in claim 3, wherein a first volume defined by the first chamber interior is greater than a second volume defined by the second chamber interior.

6. The dual-cyclonic spray chamber apparatus as recited in claim 3, wherein the second cyclonic spray chamber is oriented for directing the first conditioned portion of the aerosol at least substantially tangentially to the second chamber interior.

7. A dual-cyclonic spray chamber apparatus comprising:

a first cyclonic spray chamber for receiving an aerosol and conditioning the aerosol to separate a first conditioned portion of the aerosol from a second portion of the aerosol, the first cyclonic spray chamber defining a first chamber interior, the first cyclonic spray chamber comprising an input port in fluid communication with the first chamber interior for receiving the aerosol to be conditioned by the first cyclonic spray chamber; and a second cyclonic spray chamber coupled with the first cyclonic spray chamber, the second cyclonic spray chamber for receiving the first conditioned portion of the aerosol and further conditioning the first conditioned portion of the aerosol to separate a first further conditioned portion of the first conditioned portion of the aerosol from a second conditioned portion of the first conditioned portion of the aerosol, the second cyclonic spray chamber defining a second chamber interior, the second cyclonic spray chamber comprising an output port for expelling the first further conditioned portion of the first conditioned portion of the aerosol from the second chamber interior and a baffle at least partially disposed within the second chamber interior, the baffle defining an interior portion for receiving the first further conditioned portion of the first conditioned portion of the aerosol; and a linking chamber for coupling the first cyclonic spray chamber to the second cyclonic spray chamber, wherein the linking chamber comprises a taper and forms an annular drain portion for removing the second conditioned portion of the first conditioned portion of the aerosol from the second cyclonic spray chamber.

8. The dual-cyclonic spray chamber apparatus as recited in claim 7, further comprising a drain port in fluid communication with the first chamber interior for removing the second portion of the aerosol from the first cyclonic spray chamber.

9. The dual-cyclonic spray chamber apparatus as recited in claim 7, wherein the input port is oriented at least substantially orthogonally to the output port for expelling the first further conditioned portion of the first conditioned portion of the aerosol at least substantially orthogonally to the aerosol received at the first cyclonic spray chamber.

10. The dual-cyclonic spray chamber apparatus as recited in claim 7, wherein a first volume defined by the first chamber interior is greater than a second volume defined by the second chamber interior.

11. The dual-cyclonic spray chamber apparatus as recited in claim 7, wherein the second cyclonic spray chamber is oriented for directing the first conditioned portion of the aerosol at least substantially tangentially to the second chamber interior.

* * * * *